Dec. 22, 1959 E. H. DOERR Plant Pat. 1,890
GLADIOLUS PLANT
Filed Feb. 2, 1959
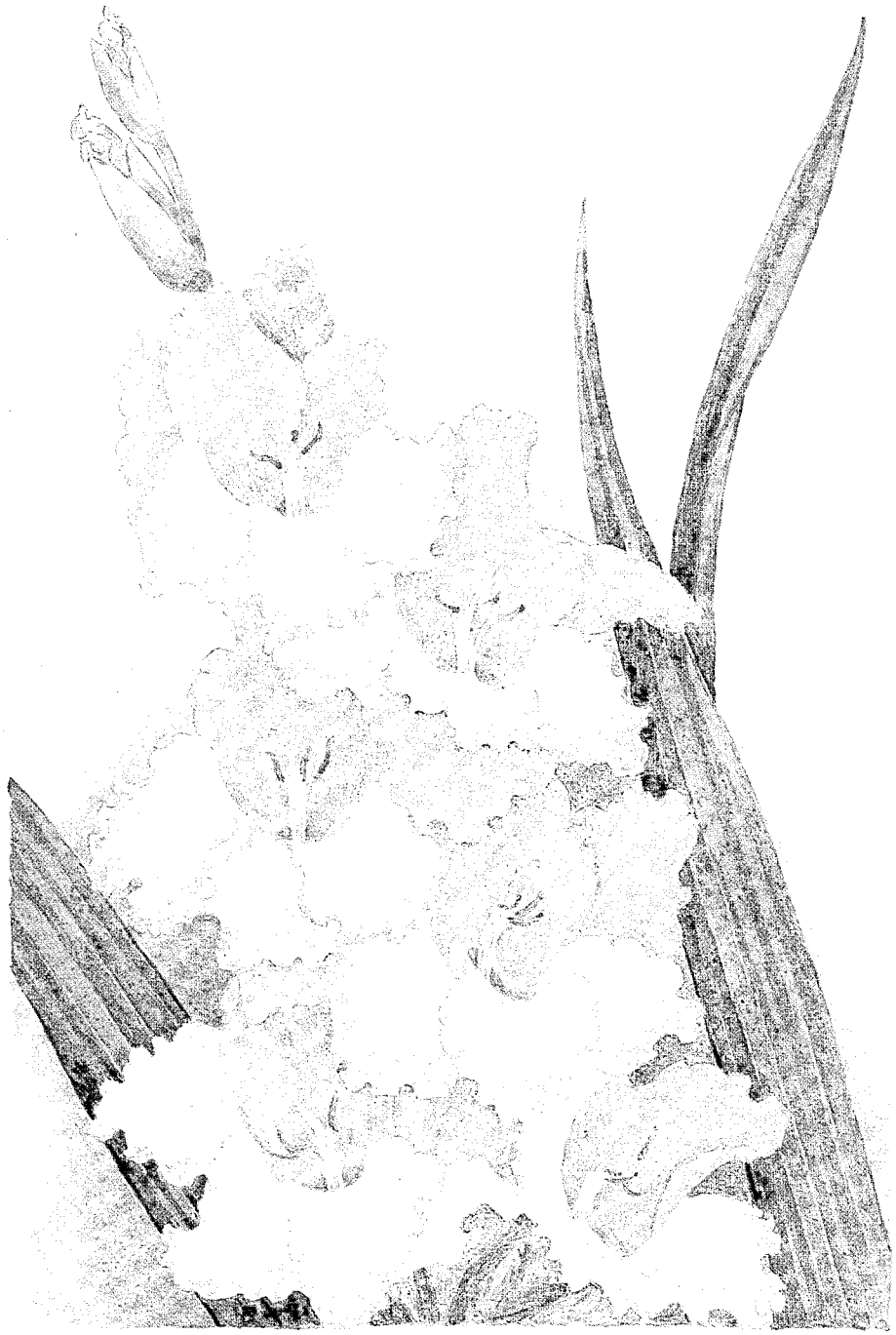
WITNESS
Addison E Avery
INVENTOR
ERVIN H. DOERR
by Rummler & Snow
ATTYS.

United States Patent Office

Plant Pat. 1,890
Patented Dec. 22, 1959

1,890

GLADIOLUS PLANT

Ervin H. Doerr, New Ulm, Minn.

Application February 2, 1959, Serial No. 790,781

1 Claim. (Cl. 47—60)

My present invention concerns a new and distinct variety of Gladiolus plant, developed by me in my nursery gardens at New Ulm, Minnesota, and is the result of breeding efforts carried on by me since 1945 with the object of producing a Gladiolus plant having improved characteristics of color and size of blooms, more vigorous growth habit, and better quality of spikes, particularly for cut flower use.

My new variety of Gladiolus originated as a seedling, identified by me as #223–1, produced from the seed parent "Ethel C. Cole" (unpatented) and the pollen parent "Elizabeth the Queen" (unpatented) and has been asexually reproduced by me from cormels, at New Ulm, Minnesota.

Continued asexual propagation of this new variety, through several generations, has demonstrated that its distinctive characteristics are fixed and that the keeping quality of its bulbs from season to season is exceedingly good.

In general the plant structure of my new variety is like that of the Gladiolus family with the flowers growing from a sturdy stem or spike and the leaves being abundant, long and sword-shaped. The plant is particularly distinctive, however, in the unusual lavender and white coloring of its many closely spaced flowers, the extraordinarily large size of the flowers, and its vigorous upright growth habit which reach to a height of about five feet. The plant blooms once, in mid-fall season. It is not affected by wet or hot weather and the flowers have excellent lasting qualities for form and color, both on the plant and as cut flowers.

The accompanying full color illustration of my new variety shows a cluster of flowers, together with leaves and partly opened buds.

The following is a further description of my new variety of Gladiolus plant:

*Flower*

Blooms: Once, in mid-season of fall.
Size: Large, 4 to 5 inches in diameter, and about 5½ inches in depth.
Borne: Singly, closely spaced along stem.
Shape: Of usual Gladiolus form.

Petalage: 6 petals, with ruffled margins.
Texture: Leathery.
Persistence: Flowers hang on stem and dry.

*Bud*

Form: Long and pointed.
Color: Lavender, when sepals first divide and when petals begin to unfurl.

*Plant*

Form: Usual Gladiolus form.
Height: About 60 inches.
Growth: Vigorous and upright.
Foliage: Abundant, sword shaped and longitudinally ribbed.

*Genital organs*

Stamens: Anthers, 3 in number.
Pollen: Dark lavender in color.
Pistils: One, about 1½ inches long.
Ovaries: Normal.

An outstanding and distinctive characteristic of my new variety of Gladiolus resides in the beautiful lavender color of the rearward petals of the blooms and the white lavender fringed coloring of the forward petals, all of which combine to provide a new and pleasing color effect. The plant produces sturdy spikes of high quality, excellent for cut flower use, and the buds open easily when the spikes are cut and placed in water.

The color designations for my new Gladiolus plant, according to Maerz and Paul's Dictionary of Color, are as follows:

| | Plate | Letter | No. |
|---|---|---|---|
| Flower: | | | |
| Main front or lower white petals | 49 | A | 1 |
| with creamy yellow throat | 9 | B | 2 |
| and light lavender margins | 49 | A | 5 |
| Upper petals—light lavender | 49 | A | 7 |
| to | 49 | A | 9 |
| Pistils | 49 | A | 1 |
| Stamens—aster color | 44 | F | 7 |
| Leaves: | | | |
| Bud sheath—light yellow green | 17 | K | 6 |
| Main leaf, medium green | 21 | L | 9 |

Having thus described my new variety of Gladiolus plant, I claim:

A new and distinct variety of Gladiolus plant substantially as herein shown and described, characterized particularly by the lavender coloring of its blooms in which the back petals are of a varying light to deep lavender color and the front petals are generally white and cream color with ruffled lavender colored margins; and further characterized by its vigorous growth, the height of its growth, the large size of its blooms, and its excellent lasting quality both on the plant and as cut flowers.

No references cited.